United States Patent [19]

Nakatsugawa et al.

[11] Patent Number: 5,143,835
[45] Date of Patent: Sep. 1, 1992

[54] ALKALOPHILIC METHANOGEN AND FAST METHANE FERMENTATION METHOD

[75] Inventors: Naoki Nakatsugawa, River-side Tsumita 303, 18-1, Shirako 3-chome, Wako-shi, Saitama-ken; Koki Horikoshi, 39-8, Sakuradai 4-chome, Nerima-ku, Tokyo, both of Japan

[73] Assignees: Research Development Corporation of Japan, Tokyo; Naoki Nakatsugawa, Wako; Koki Horikoshi, Tokyo, all of Japan; a part interest

[21] Appl. No.: 318,907

[22] Filed: Mar. 6, 1989

[30] Foreign Application Priority Data

Mar. 7, 1988 [JP] Japan .................................. 63-53294
Mar. 7, 1988 [JP] Japan .................................. 63-53295

[51] Int. Cl.$^5$ .......................... C12P 5/02; C12N 1/20; C02F 3/00
[52] U.S. Cl. ............................... 435/167; 435/252.1; 210/603
[58] Field of Search ............................ 435/167, 252.1; 210/603

[56] References Cited

PUBLICATIONS

Zhilina et al, Microbiology, (USSR) 1979, vol. 48, pp. 223–228.
Archer et al, FEMS Microbiology Letters, 16 (1983) pp. 5217–5223.
International Journal of Systematic Bacteriology, vol. 36, No. 3, Jul. 1986, pp. 380–382, S. Worakit et al: "Methanobacterium alcaliphilum sp.nov., an $H_2$-utilizing methanogen that grows at high pH values."
Patent Abstracts of Japan, vol. 4, No. 19 (C-73), Feb. 16, 1980, & JP-A-54 154 597.
Dissertation Abstracts Int. B, vol. 32, No. 9, 1972, p. 5238, G. H. Toenniessen: "Studies on acetate and methanol fermenting methanogenic enrichments."

*Primary Examiner*—Irene Marx
*Attorney, Agent, or Firm*—Oblon, Spivak, McClelland, Maier & Neustadt

[57] ABSTRACT

*Methanosarcina alcaliphilum* which is alkalophilic methanogen having the optimum growth pH range of from about 8.1 to about 8.7. This strain exhibits excellent properties such as alkalophilicity and resistance to low temperature. This strain makes it possible to carry out methane fermentation methods at an alkaline pH and at a low temperature conditions. This strain is applied to methane fermentation in treating solid waste and waste water. Moreover, the bacterial concentration thereof in a reactor can be increased within a very short time and, therefore, the size of such a reactor can be made compact.

7 Claims, 4 Drawing Sheets

ALKALOPHILIC METHANOGEN AND FAST METHANE FERMENTATION METHOD

BACKGROUND OF THE INVENTION

1. Field of the Invention

The present invention relates to alkalophilic methanogen and more particularly to *Methanosarcina alcaliphilum* having an optimum growth pH ranging from about 8.1 to about 8 7.

In addition, the present invention also relates to a methane fermentation method in which methanogens are used and more specifically to a method for carrying out methane fermentation at a high speed by increasing the bacterial concentration of methanogens in a reactor for methane fermentation within a short period, through the best use of the properties of the methanogens.

2. Description of the Prior Art

Heretofore, there have been known the following 5 bacterial species as methanogens belonging to genus Methanosarcina: *Methanosarcina barkeri* (see Microbiological Reviews, 1979, Vol. 43, pp. 260-296 and FEMS Microbiology Letters, 1983, Vol. 16, pp. 217-223); *Methanosarcina acetivorans* (see Applied and Environmental Microbiology, 1984, Vol. 47, No.5, pp. 971-978); *Methanosarcina vacuolata* (see Microbiology, U.S.S.R., 1979, Vol. 48, pp. 279-285); *Methanosarcina thermophila* (see International Journal of Systematic Bacteriology, 1985, Vol. 35, No.4, pp. 522-523); and *Methanosarcina mazei* (see Current Microbiology, 1980, Vol. 3, pp. 321-326).

However, not all of these methanogens are alkalophilic and their optimum growth pH condition is less than 7.5. There have not so far been discovered any bacteria having a high optimum growth pH in the order of not less than 7.5 to 8.0 and belonging to the genus Methanosarcina.

On the other hand, the following two bacterial species belonging to genus Methanobacterium have been known as alkalophilic methanogens: *Methanobacterium alcaliphilum* (see International Journal of Systematic Bacteriology, 1986, Vol. 36, No.3, pp. 380-382) and *Methanobacterium thermoalcaliphilum* (see Archives of Microbiology, 1985, Vol. 142, pp. 211-217).

However, both of these alkalophilic methanogens are rod-shaped belonging to genus Methanobacterium and they can utilize only hydrogen and carbon dioxide as substrates.

As described above briefly, alkalophilic methanogens discovered heretofore can simply assimilate hydrogen and carbon dioxide as the substrate and they belong to genus Methanobacterium or they have morphological properties of rods.

Besides, methane fermentation methods have been utilized widely for treating waste water and solid waste from the viewpoint of effective use of biomass, biogas production or the like.

Nevertheless, the conventionally known methanogens used in methane fermentation methods are strictly anaerobic bacteria and show extremely slow rate of growth. For this reason, the use of a large-scale reactor for methane fermentation is required and likewise it takes a long period of time to obtain bacterial concentration of the methanogens in the reactor which is required for maintaining a stable steady state of methane fermentation.

There has been proposed a method which comprises the step of controlling conditions in the reactor such as pH and temperature for the purpose of improving the efficiency of the foregoing methane fermentation. However, such a control of only the environmental conditions enables such a method to be speeded up only slightly and permits an improvement of efficiency only to a limited level.

In particular, in the methane fermentation methods for treating solid waste and/or waste water, main substrates are acetic acid and $H_2/CO_2$ (among the substrates capable of being assimlated by methanogens, acetic acid and $H_2/CO_2$ are exclusively present in such waste). However, the assimilation rate of acetic acid by methanogens is very low and this serves as a rate-determining step. Thus, it takes a long period of time to start the methane fermentation reactor and the volume of the reactor must be enlarged. Morever, the reactor is started according to adaptation-cultivation method using substrates inherent to the bacteria used.

SUMMARY OF THE INVENTION

Accordingly, an object of the present invention is to provide alkalophilic bacteria belonging to genus Methanosarcina having an optimum growth pH range higher than those of the aforesaid methanogens belonging to genus Methanosarcina.

Another object of the present invention is to provide alkalophilic methonogens which is capable of utilizing substrates other than hydrogen and carbon dioxide and which has morphological properties differing from rods, or which belongs to genus other than genus Methanobacterium.

A further object of the present invention is to provide a methane fermentation method which can provide methane at a high speed and high efficiency.

A still further object of the present invention is to provide a methane fermentation method which makes it possible to increase the bacterial concentration in a reactor within a short period of time, utilizing bacteriological properties of methanogens.

According to an aspect of the present invention, there is provided *Methanosarcina alcaliphilum* which is alkalophilic methanogen having an optimum growth pH ranging from about 8.1 to about 8.7.

According to another aspect of the present invention, there is provided a methane fermentation method which comprises culturing methanogens in a culture medium containing substrates as principal subject of fermentation which are assimilated by the bacteria at a slow assimilation rate (in other words, at slow generation time), the method characterized in that the methanogens are capable of utilizing at least two substrates and they utilize the substrates at different rates and that the culture or fermentation is carried out in the presence of the substrates which are assimilated at a slow rate and substrates which are utilized at a rate faster than that of the former (i.e., at a short generation time).

BRIEF EXPLANATION OF THE DRAWINGS

The present invention will hereunder be explained in more detail with reference to the accompanying drawings, wherein.

DETAILED EXPLANATION OF THE INVENTION

Figure 1:
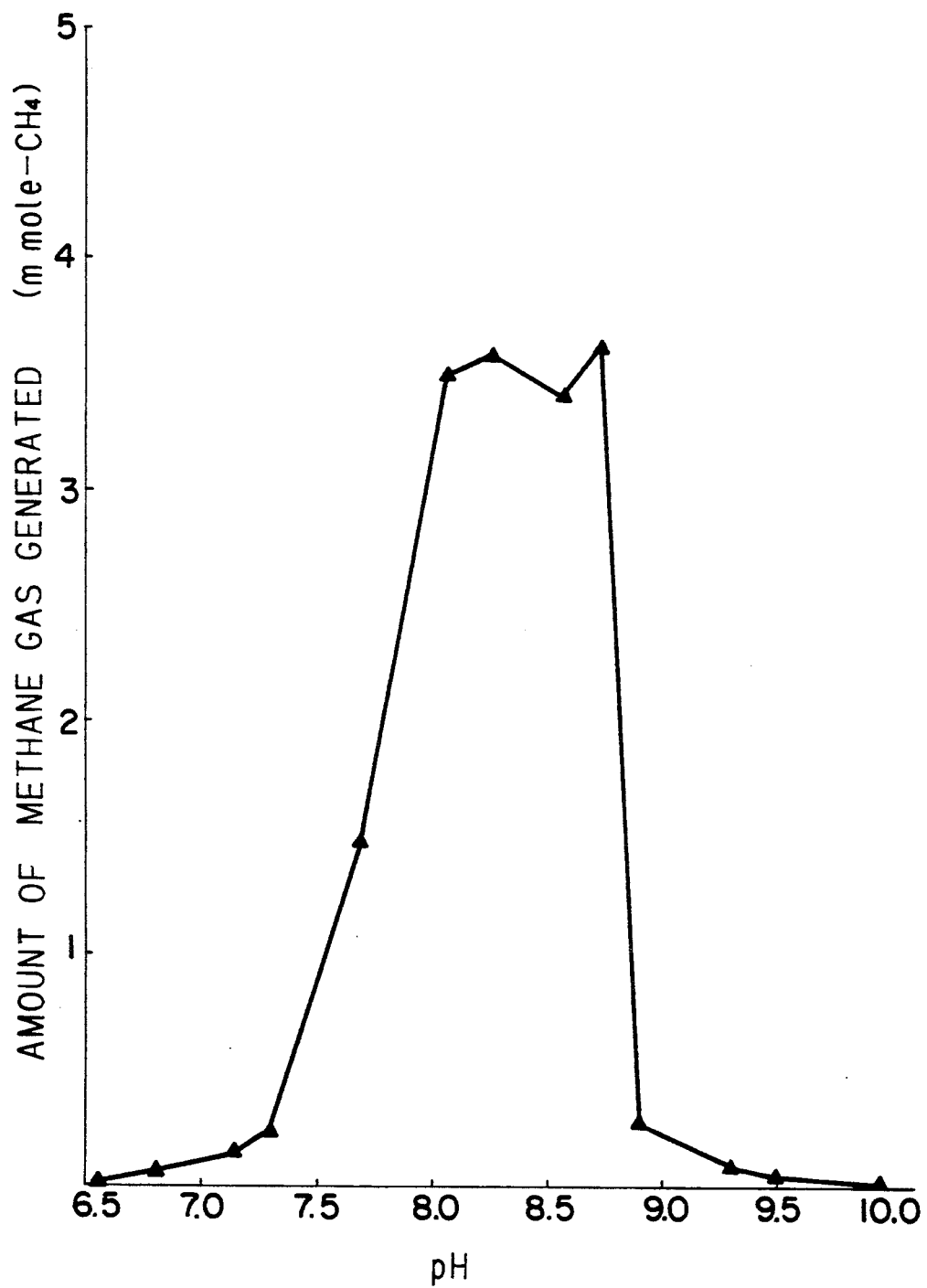
FIGS. 1 to 3 are graphs in which the amount of methane generated is plotted against the value of pH, culture temperature and the kinds of substrates respectively, observed when the methanogen NY-728 of the invention is used.

*Methanosarcina alcaliphilum* (NY-728) of the present invention is deposited with FERMENTATION RESEARCH INSTITUTE (FRI) 1-1-3, Yatabe-Machi, Tsukuba-gun, Ibaraki-Ken, Japan under the accession number of FERM BP-2309 on Mar. 4, 1988. The deposit was made under the Budapest Treaty, and all restrictions on the availability to the public of the deposited microorganism will be irrevocably removed upon the granting of a patent.

The invention will hereunder be explained in more detail.

(1) Screening Method

In the invention, screening of methanogenic bacteria is performed according to the method for isolating anaerobic bacteria as disclosed in Japanese Patent Application Serial (hereunder referred to as "J.P.A.") No.61-191541 (corresponding to J.P. Disclosure No.63-49074) and Japanese Utility-Model Application Serial (hereunder referred to as "J.UM.A." No.61-125086 (corresponding to J.UM. Disclosure No.63-31799). More specifically, the screening method comprises exploring soil in special environment such as strong alkaline environment and those having high salts' concentration to obtain soil under the intended special environmental conditions, rapidly establishing desired conditions such as anaerobic conditions and low oxidation redox potential conditions required for the bacteria collected utilizing a solution for dilution which has a basic composition similar to those disclosed in J.P.A. No.61-191541, then preparing a solution for dilution while taking, into consideration, conditions of environment from which the soil is collected, such as pH and concentrations of salts and immediately suspending the soil in the dilution solution. The resultant suspension is maintained in a container as disclosed in J.UM.A. No.61-125086 so that the anaerobic bacteria, i.e., methanogens do not die out and hence the interested methanogenic bacteria from a special environment do not likewise die out, in order to transport the same. This transported sample is used as a sample for isolation culture.

Regarding the soil source for such screening, any soil in special environment is widely explored in Japan and abroad.

(2) Isolation Culture

As culture mediums for isolation culture, an isolation medium which has been developed originally by the inventors of this invention is employed. The composition thereof is shown in the following Table I. Moreover, compositions of the solution of trace elements and the solution of vitamins listed in Table I are summarized in Tables II and III respectively. Regarding the solution of trace elements shown in Table II, the solution in which the kinds and the amount of the trace elements to be added to the solution are strengthened is used in the invention since the requirements of the interested bacteria for trace elements are not clear.

As the substrates in the culture medium, sodium formate, sodium acetate, methanol and methylamine are used in an amount ranging from 0.5 to 1.0%, respectively as shown in Table I. The pH value of the medium at the beginning of the culture is controlled with sodium bicarbonate.

In addition, since the methanogens are archaebacteria and do not include peptidoglycan in the cell wall, they exhibit no sensitivity to peptidoglycan synthesis inhibiting agents. Morever, they do not have sensitivity to protein synthesis inhibiting agents effective to bacteria which have 70S ribosome system of procaryotic cell type though their ribosome is 70S type one. Thus, effective isolation of the desired methanogens is carried out by adding, to the culture medium, an antibiotic which can suppress the growth of only non-methanogenic bacteria during the isolation culture. More specifically, vancomycin which is an agent for inhibiting peptidoglycan synthesis in the cell wall and kanamycin which is a protein synthesis inhibiting agent effective to bacteria having procaryotic cell type 70S ribosome system are practically employed as shown in Table I.

As the gas phase during culture, there are used three kinds of gases i.e., $H_2/CO_2$ (80/20) mixed gas, $N_2/CO_2$ (80/20) mixed gas and $N_2$ gas which are deoxygenated prior to use. Such a gas is charged into a container for culture so that the pressure therein is equal to 2 atoms (positive) during culture irrespective of the kinds of the culture medium which may be either liquid medium or agar medium, whereby the culture is carried out under press. Moreover, the culture is principally performed in accordance with standing culture or culture in the dark.

As explained above, the methanogenic bacteria growing under special conditions have widely been explored. Conditions other than those discussed above during the isolation culture are as follows: pH=6.5 to 10.0; temperature=10° to 60° C.

(3) Identification of the Objective Bacteria

The identification of the objective methanogens growing under special environment is carried out as follows: Culture is performed according to the aforementioned isolation culture technique at a desired temperature utilizing a culture medium in which conditions such as pH and the kinds and concentration of substrates used are adjusted and to which there are added the aforesaid agent for inhibiting peptidoglycan synthesis in the cell wall and an antibiotic as an agent for inhibiting protein synthesis effective to bacteria having procaryotic cell type 70S ribosome system in order to isolate only the methanogens belonging to archaebacteria. The methanogens which would grow during such isolation culture are considered to be one of the following bacteria, so far as can be judged from the conditions of the culture medium such as those listed above:

(a) Objective methanogens;
(b) Strictly anaerobic bacteria, which are antibiotic resistant, other than methanogenic bacteria; or
(c) Archaebacteria other than methanogens, which are strictly anaerobic or resistant to anaerobic conditions.

The following two methods are adopted to identify only the objective methanogens from product of the isolation culture: one of which comprises analyzing gases present in the head space of the container for culture by a means such as gas chromatography to confirm the production of methane gas (those producing methane gas are methanogens; and the other of which comprises observing the grown bacteria by a fluorescent microscope to examine the product. In the latter, the methanogens have a factor F 420 inherent thereto and emit fluorescent rays of bluish green originated from the factor when they are irradiated with ultraviolet rays of long wave length. Therefore, it can be confirmed whether the grown bacteria are methanogenic ones or non-methanogenic ones on the basis of the presence or absence of the emission of fluorescent rays upon irradiating them with ultraviolet rays and examining them with a fluorescent microscope. In this regard, some of the non-methanogenic bacteria emit fluorescent rays, but the fluorescent rays emitted by them are not rays of bluish green but those of yellowish white or bluish white. Thus, in such cases, the methanogenic bacteria may certainly be distinguished from the non-methanogenic ones.

The objective methanogenic bacteria can be isolated in pure culture by identifying them in accordance with the foregoing methods and then repeating procedures such as dilution and agar plating methods to purify the same.

TABLE I

Composition of Culture Medium

| Component | Amount (g/l) | |
|---|---|---|
| Dipotassium hydrogenphosphate | 0.7 | |
| Ammonium chloride | 1.0 | |
| Calcium chloride | 0.1 | |
| 2-Mercaptoethane sulfonic acid | 1 | (mg) |
| Yeast extract (available from Difco Co., Ltd.) | 1.0 | |
| Triputicase peptone (available from B.B.L. Co., Ltd.) | 1.0 | |
| Casamino acid (available from Difco Co., Ltd.) | 0.5 | |
| Cacitone (available from Difco Co., Ltd.) | 1.0 | |
| Solution of trace elements (see Table II) | 10 | (ml) |
| Solution of vitamins (see Table III) | 10 | (ml) |
| Resazurin | 1 | (mg) |
| L-Cystein | 0.45 | |
| Sodium sulfide | 0.65 | |
| Vancomycin | 0.5 | |
| Kanamycin | 0.5 | |
| Sodium chloride | 1 | |
| Magnesium chloride | 0.2 | |
| Sodium formate | 5 to 10 | |
| Sodium acetate see the remark *1) | 5 to 10 | |
| Methanol | 5 to 10 | |
| Trimethylamine hydrochloride | 5 to 10 | |

*1): In each culture medium, only one of these substrates was used;
*2): In each culture medium, the pH value was adjusted with the addition of sodium bicarbonate;
*3): Each numerical value in Table I denotes the content of each component per liter of the culture medium in which the balance was purified water.

TABLE II

Composition of the Solution of Trace Element

| Component | Amount (g/l) |
|---|---|
| Ferrous sulfate | 0.3 |
| Cobalt chloride | 0.2 |
| Zinc chloride | 0.1 |
| Boric acid | 0.05 |
| Sodium molybdate | 0.2 |
| Manganese chloride | 0.1 |
| Copper sulfate | 0.01 |
| Aluminum potassium sulfate | 0.005 |
| Nitrilotriacetic acid | 2.5 |
| Nickel chloride | 0.5 |
| Sodium selenite | 0.1 |
| Sodium tungstate | 1.0 |
| Cadmium chloride | 0.05 |

*): Each numerical value in Table II denotes the content of each component per liter of the solution of trace elements in which the balance was purified water.

TABLE III

Composition of the Solution of Vitamin

| Component | Amount (mg/l) |
|---|---|
| Biotin | 2 |
| Folic acid | 2 |
| Pyridoxine | 10 |
| Riboflavin | 5 |
| Thiamine | 5 |
| Pantothenic acid | 5 |
| Cyanocobalamin | 0.1 |
| p-Aminobenzoic acid | 5 |
| Alpha-lipoic acid | 5 |

*): Each numerical value in Table III denotes the content of each component per liter of the solution of vitamins in which the balance was purified water.

(4) Collection of the Objective Microorganisms

The inventors of this invention tried to isolate desired methanogenic bacteria from soil in special environmental conditions widely collected in Japan and abroad in accordance with the aforementioned methodology. As a result, a variety of alkalophilic methanogens were isolated from soil matter collected from the bottom of lakes and marches in Tohoku District of Japan.

These methanogens were cultured and examined. Among these methanogens, there was isolated alkalophilic methanogen having the highest optimum growth pH (strain NY-728).

The strain NY-728 grows at a wide range of pH at least ranging from about 7.1 to about 9.2 and has the optimum growth pH ranging from about 8.1 to about 8.7 and good methane gas production acitivity. It was, therefore, confirmed that the strain is alkalophilic one. It was likewise confirmed that the methanogen NY-728 according to the present invention is alkalophilic as described above, that the optimum growth temperature ranges from about 34° to 42° C. and that it maintains methane production activity within a wide range of temperature at least ranging from about 15° to 45° C.

It is confirmed that individual cells of NY-728 are coccus having a diameter ranging from 1.7 to 2.7 mircon and they have morphological properties of sarcina. It is also confirmed that this strain is gram-negative and strictly anaerobic, which never causes sporulation, that unlike the general bacteria, it is archaebacterium exhibiting no sensitivity to antibiotics or the like which inhibit the peptidoglycan synthesis in cell wall and that it has ether bonds inherent to membrane lipid of the archaebacteria.

It is confirmed that the strain NY-728 is capable of utilizing hydrogen and carbon dioxide, acetic acid, methanol and methylamine at a cultivation temperature of 37° C. and that the methane production activity thereof is also good.

In addition, when the strain is cultured in the presence of methanol as the substrate among others which can be assimilated by the strain, the maximum generation time thereof is about 4 hours. Thus, it is confirmed that the strain shows extremely fast propagation rate compared with that observed when it is cultured in the presence of other substrates.

The methane fermentation method of the present invention will hereunder be explained in more detail.

In the method of the present invention, there are employed methanogens which are capable of utilizing at least two substrates and which utilize these substrates at different assimilation rates.

Examples of such methanogens include those belonging to genus Methanosarcina. Specific examples of such methanogens are listed in the following Table IV.

The method of the present invention produces methane by culturing the aforementioned methanogens in the presence of substrates as principal subject of fermentation which are assimilated by the bacteria at a low assimilation rate and carrying out the culture or the fermentation in the presence of the substrates which are assimilated at a low assimilation rate and substrates which are assimilated at a rate faster than that of the former.

For instance, when *Methanosarcina acetivorans* C2A is cultured at a temperature of 35° to 40° C., the generation time thereof is 24.1 hours for acetic acid as a substrate; 5.2 hours for methanol; and 6.7 to 7.3 hours for methylamine. Therefore, when *Methanosarcina acetivorans* C2A is used as methanogens, acetic acid or methylamine may be used as the substrate which is assimilated at a low rate.

If acetic acid is used as the substrate which is assimilated at a low rate, methanol, methylamine or a mixture thereof may be used as the substrate assimilated at a high rate. On the other hand, when methylamine is used as the substrate assimilated at a low rate, methanol may be used as the substrate assimilated at a high rate.

In addition, when *Methanosarcina thermophila* TMI (whose generation time at 50° C. is 12 hours for acetic acid; and 7 to 10 hours for methanol) is used as the methanogen, the method of the present invention can be carried out using methanol as the substrate which is assimilated at a high rate if acetic acid is used as the substrate assimilated at a low rate.

The method of the present invention can likewise be carried out in the same manner as above, when *Methanosarcina alcaliphilum*, (whose generation time at 37° C. is 19 hours for $H_2/CO_2$; 17 hours for acetic acid; 4 hours for methanol; and 6 hours for methylamine) is used as the methanogen. For instance, when $H_2/CO_2$, acetic acid or a mixture thereof is used as the substrate which is assimilated at a low rate, methanol, methylamine or a mixture thereof may be used as the substrate which is assimilated at a high assimilation rate.

The method of the present invention can be performed in the presence of one or more of substrates which are assimilated at a low assimilation rate and one or more of the substrates which are assimilated at a high assimilation rate, simultaneously.

Time for introducing, into a reaction system, the substrate assimilated at a high rate and the amount thereof may vary depending on factors such as the scale of the fermentation bath. For instance, the starting time of the reaction can extremely be reduced by adding it at the beginning of the fermentation.

Conditions of fermentation may appropriately be varied depending on the kinds of the methanogens and the fermentation may be carried out according to the conventional methods.

The method of the present invention can be applied to not only the methane fermentation in treating solid waste and waste water but also the methane fermentation in all the other fields.

Methanogens are used as the microorganisms playing central role in the methane fermentation (bio-methanation) widely employed for the purposes of efficient use of biomass and biological gas production. If the novel methanogen of the present invention is applied to the conventional methane fermentation techniques, such a technique would make rapid progress since the strain of the prsent invention exhibits excellent properties such as alkalophilicity and high resistance to low temperature. More specifically, the methods of methane fermentation are commonly carried out at around neutral pH region and a medium temperature of 37° C., but it becomes possible to carry out these methods at an alkaline pH and low temperature conditions if the methanogen of the present invention is used. This, in turn, makes it possible to use a wide variety of biomass waste in such a method of methane fermentation as well as to provide a highly efficient methane fermentation method.

For instance, the conventional method of methane fermentation must be carried out in the vicinity of neutral pH, and for this reason if pH of the substrate to be used is high, a large amount of pH adjusting agents are in general added to a bioreactor. Such a problem associated with the conventional methods can effectively be solved through the use of the methanogen of the invention.

In addition, if the methanogen of this invention is used in breeding by a genetic engineering technique, as the source of genes encoding properties favorable or resistant to special environment, such as alkalophilicity and resistance to low temperature, it would be possible to effectively carry out the practical methane fermentation or to efficiently produce other useful substances.

The methane fermentation method of the present invention makes it possible to increase the bacterial concentration of the methanogen in a reactor within a very short time. Therefore, the size of the reactor can be made compact substantially, by the use of such methanogen. In addition, the time required for establishing a desired bacterial cell number in the reactor can also be reduced substantially and thus a stable steady state of methane fermentation can be maintained.

The present invention will hereunder be described in more detail with reference to the following non-limitative working Examples and the effects practically achieved will also be discussed in detail in comparison with Comparative and Reference Examples given below.

EXAMPLE 1

The screened and isolated strain (NY-728) was cultured in a medium whose pH was changed and the results obtained were plotted on the attached FIG. 1. More specifically, the strain (NY-728) of the present invention was cultured at 37° C. for 5 days utilizing mediums listed in Table 1 in which methanol was used as the substrate in an amount of 0.8% and pH thereof was changed within the range of 6.5 to 10.0.

In FIG. 1, the results obtained are plotted with pH of the medium as abscissa and the amount of methane gas produced (mmoles) as ordinate. The data plotted on FIG. 1 indicate that the strain NY-728 grows at least at a pH ranging from 7.1 to 9.3 and have an optimum growth pH ranging from 8.1 to 8.7.

EXAMPLE 2

Figure 2:
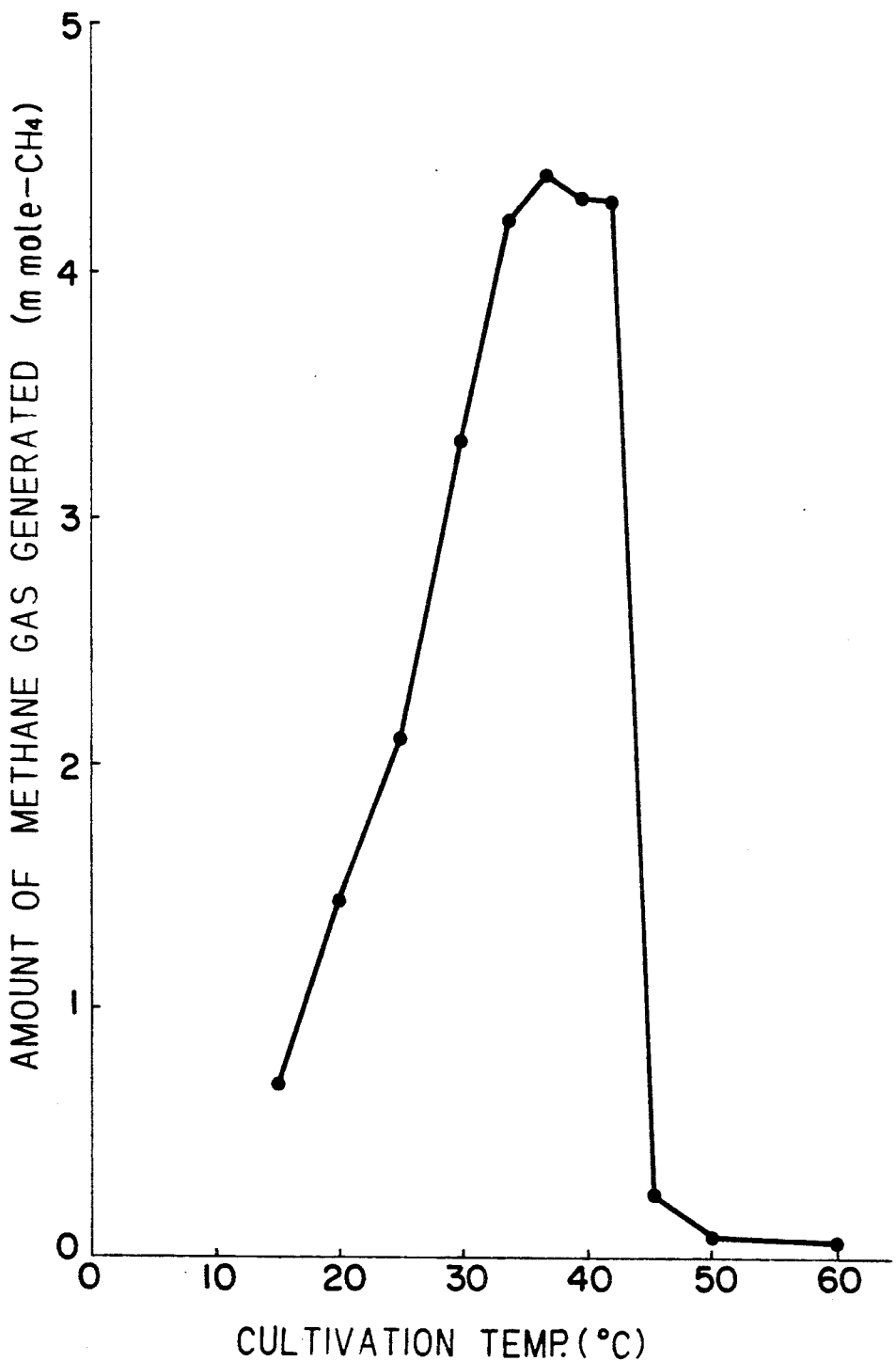

The screened and isolated strain (NY-728) of the present invention was cultured in a medium whose temperature was changed and the results obtained were plotted on the attached FIG. 2. More specifically, the strain (NY-728) was cultured at a temperature ranging from 15° to 60° C. for 20 days utilizing mediums listed in Table I in which methanol was used as the substrate in an amount of 0.8%.

In FIG. 2, the results obtained are plotted with the cultivation temperature as abscissa and the amount of methane gas produced (mmoles) as ordinate. The data plotted on FIG. 2 indicate that the strain NY-728 grows at a wide temperature range falling within the range of at least about 15° to 45° C. and have the optimum growth temperature ranging from about 34° to 42° C.

strates; morphological features; gram-staining properties; generation time; optimum growth temperature and optimum growth pH are summarized in Table IV given below in comparison with those of known methanogens.

TABLE IV

| Name of Bacteria (accession No.) | Substrate Assimilation Properties | | | | | Morphology | Gram-stain | Optimum Temp °C. | Optimum pH | Generation Time (h) |
|---|---|---|---|---|---|---|---|---|---|---|
| | $H_2/CO_2$ | HCOOH | MeCOOH | MeOH | $MeNH_2$ | | | | | |
| (i) Known methanogens belonging to genus Methanosarcina | | | | | | | | | | |
| Methanosarcina barkeri MS (DSM 800[7]) *1) | + | − | + | + | + | sarcina | + | 40 | 7.0 | 12 |
| Methanosarcina barkeri 227 (DSM 1538) *1) | + | − | + | + | + | " | + | 35 | 7.0 | 24 |
| Methanosarcina barkeri UBS (DSM 1311) *1) | + | − | + | + | + | " | + | 30 | 7.4 | 30 |
| Methanosarcina barkeri DM *1) | + | − | + | + | + | " | + | 37 | 7.0 | 28 |
| Methanosarcina barkeri FRI (DSM 2256) *2) | + | − | + | + | + | " | + | 35 | — | 33 |
| Methanosarcina acetivorans C2A (DSM 2834[T]) *3) | − | − | + | + | + | " | − | 35–40 | 7.0 | 5.2 |
| Methanosarcina vacuolata Z (DSM 1232) *4) | + | − | + | + | + | " | + | 40 | 6.5–7.0 | — |
| Methanosarcina thermophila TMI (DSM 1825[T]) *5) | − | − | + | + | + | " | + | 50 | 7.5 | 5 |
| Methanosarcina mazei (DSM 2053) *6) | − | − | + | + | + | " | ± | 30–40 | 6.0–7.0 | 7.7 |
| (ii) Known alkalophilic methanogens | | | | | | | | | | |
| Methanosarcina alcaliphilum $WeN_4$ *7) | + | − | − | − | − | coccus | − | 37 | 8.1–9.1 | — |
| Methanosarcina thermo-alcaliphilum Ac60 *8) | + | − | − | − | − | " | − | 58–62 | 7.5–8.5 | — |
| (iii) Present invention | | | | | | | | | | |
| Methanosarcina alcaliphilum NY-728 (FERM BP-2309) | + | − | + | + | + | sarcina | + | 34–42 | 8.1–8.7 | 4 |

*1): Microbiological Reviews, 1979, Vol. 47, pp. 270–296;
*2): FEMS Microbiology Letters, 1983, Vol. 16, pp. 217–223;
*3): Applied and Environmental Microbiology, 1984, Vol. 47, No.5, pp. 971–978;
*4): Microbiology (U.S.S.R.), 1979, Vol. 48, pp. 279–285;
*5): International Journal of Systematic Bacteriology, 1985, Vol. 35, No.4, pp. 533–523;
*6): Current Microbiology, 1980, Vol. 3, pp. 321–326;
*7): International Journal of Systematic Bacteriology, 1986, Vol. 36, No.3, pp. 380–382;
*8): Archives of Microbiology, 1985, Vol. 142, pp. 211–217.

EXAMPLE 3

Figure 3:
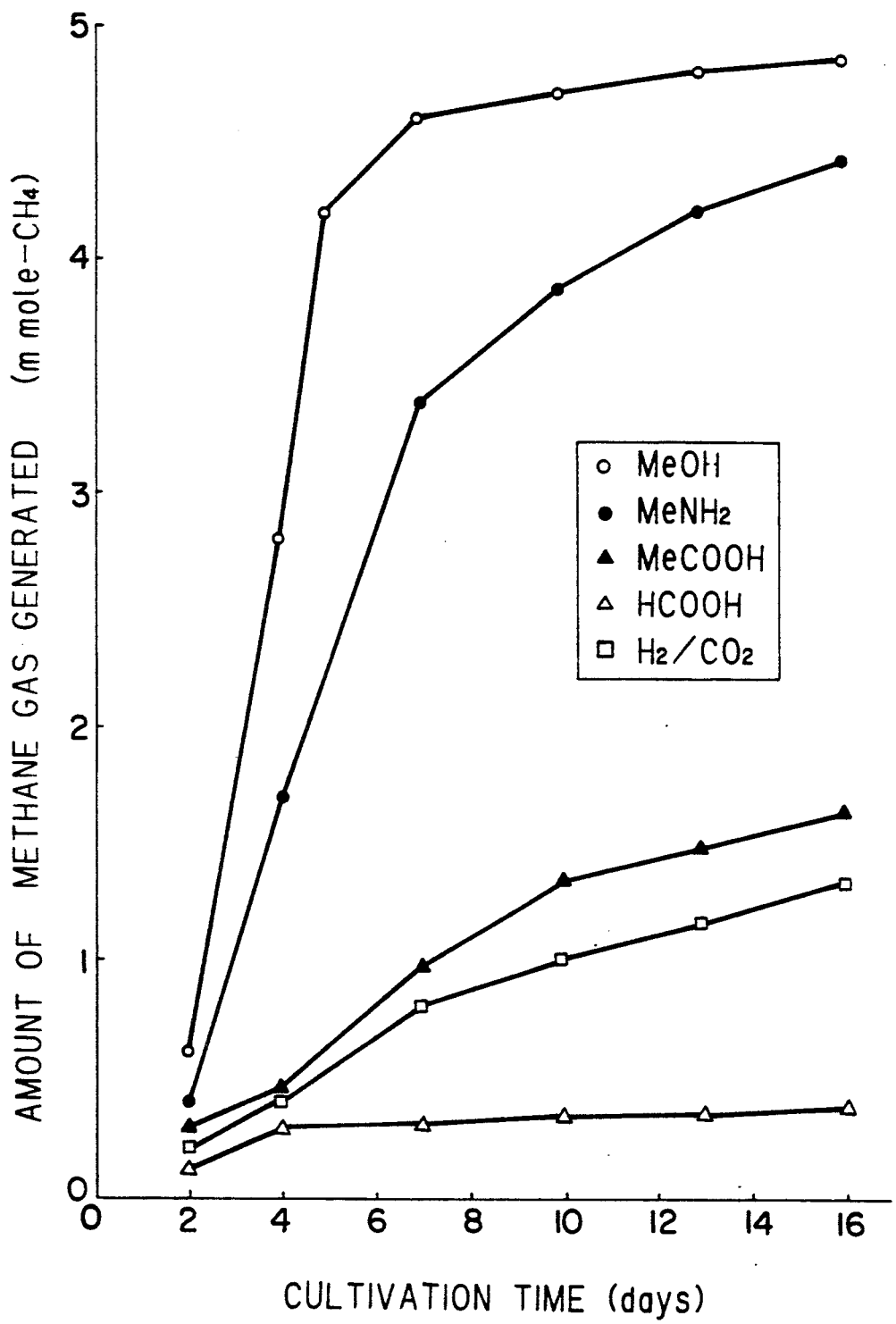

The screened and isolated strain (NY-728) of the present invention was cultured in the medium listed in Table I in which either one of sodium formate, sodium acetate, methanol and trimethylamine as a substrate and the results obtained were plotted on FIG. 3. In this respect, the concentration of the substrate was 0.8% and the gas phase for culture was $N_2$ (2 positive atms.). When the substrate used was $H_2/CO_2$, it was not added to the culture medium, but was used as the gas phase (2 atm.; positive). In this Example, pH was 8.3 and the cultivation temperature was 37° C.

EXAMPLE 4

The screened and isolated strain (NY-728) of the invention was cultured in the medium whose composition was shown in Table I and in which methanol was used as the substrate in an amount of 0.8% to estimate the generation time from the amount of methane gas generated. The generation time was found to be 4 hours.

In order to make clear that the alkalophilic methanogen of the present invention is novel methanogen which can clearly be distinguished fron known ones, properties of the strain NY-728 such as assimilation of sub- As seen from the data summarized in Table IV, it is found, in the light of the following facts, that the strain methanogen NY-728 of the present invention is a novel methanogen belonging to genus Methanosarcina:

(1) It is clear that the methanogenic strain NY-728 of the present invention belongs to genus Methanosarcina in the light of their morphological properties and substrate assimilation properties. However, the strain NY-728 is alkalophilic one having the optimum growth pH range higher than those of known bacteria belonging to genus Methanosarcina.

(2) There is not conventionally known any alkalophilic methanogen which maintains methane production activity even at a temperature as low as 15° to 20° C., but the methanogenic strain NY-728 of the present invention maintains methane gas production activity at such a low temperature condition. In other words, the strain NY-728 is resistant to low temperature.

(3) All the known alkalophilic methanogens are coccus but not sarcina. However the methanogenic strain NY-728 of the invention is sarcina in morphology.

(4) All the known alkalophilic methanogens have no ability of assimilating substrates other than hydrogen and carbon dioxide, but the methanogenic strain NY-728 of the invention can utilize acetic acid, methanol and methyl amine other than $H_2/CO_2$.

EXAMPLE 5

*Methanosarcina alcaliphilum* NY-728 (FERM BP-2309) was cultured in one liter of the medium whose composition was shown in Table I in which methanol was used as the substrate in an amount of 0.8%, at 37° C. and a pH of 8.3 for 9 days, then sodium acetate was added to the medium so that the concentration thereof was 0.8% and the culture was continued. The change in the amount of methane gas generated (mmoles-$CH_4$) with time is plotted on FIG. 4.

COMPARATIVE EXAMPLE 1

The same procedures as in Example 5 were repeated except that a medium containing 0.8% sodium acetate was used instead of the medium containing 0.8% methanol and the culture was continued for 16 hours (in the course of the culture, sodium acetate was not added to the medium). The results observed are plotted on FIG. 4.

REFERENCE EXAMPLE 1

*Methanosarcina barkeri* UBS (DSM 1311) was cultured, for 16 days, in one liter of the mediums (pH 7.4; Temp.=37° C.) having the compositions listed in Table I and containing 0.8% methanol and 0.8% sodium acetate as the substrate respectively. The results obtained are plotted on FIG. 4.

Figure 4:
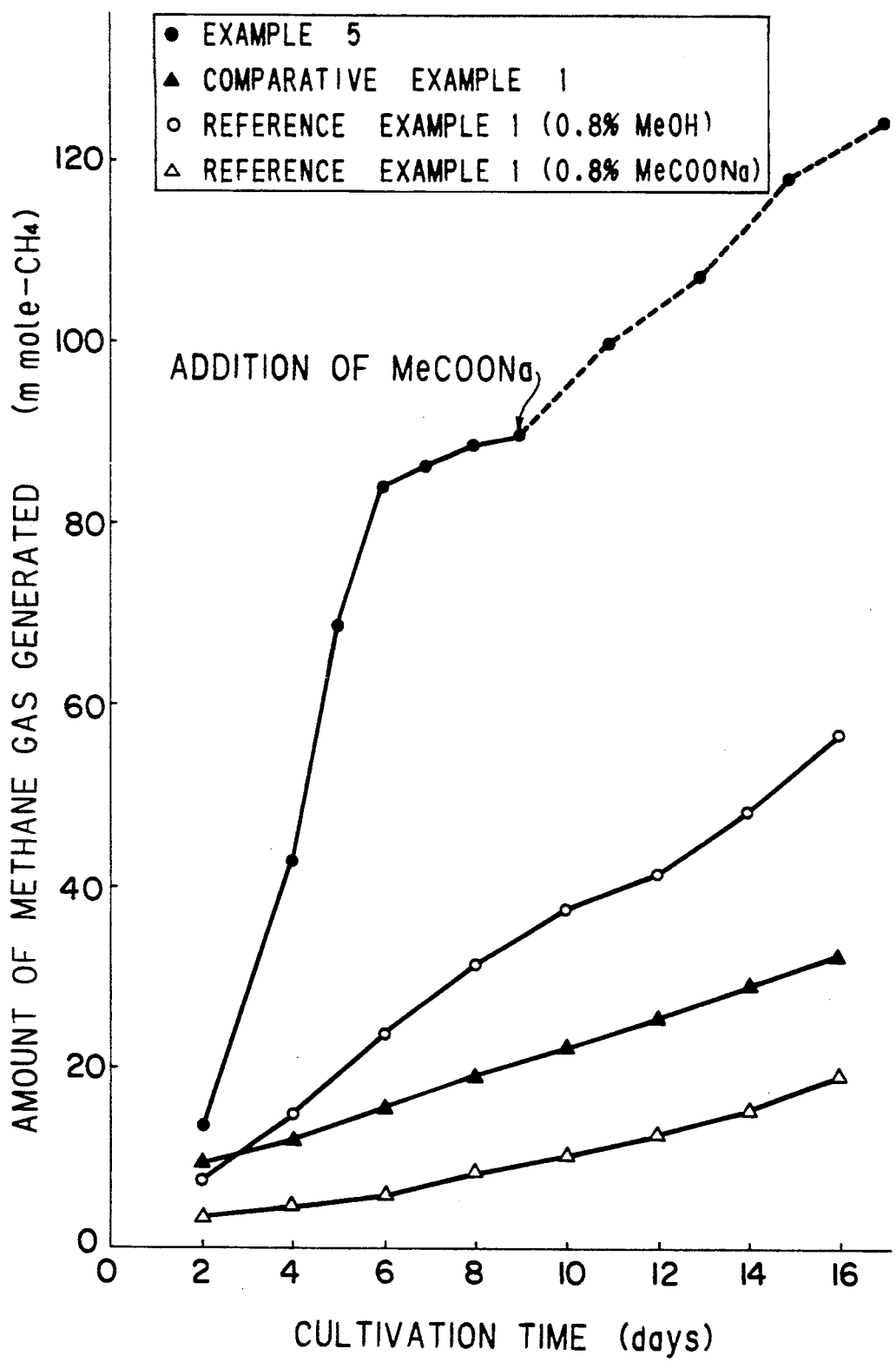
FIG. 4 is a diagram illustrating the change in the amount of methane gas generated with time.

As seen from the data plotted on FIG. 4, the amount of methane gas generated during culturing the methanogen of the present invention is substantially increased compared with those observed in Comparative and Reference Examples.

What is claimed is:

1. A biologically pure culture of *Methanosarcina alcaliphilum* NY-728 (FERM BP-2309) which is an alkalophilic methanogen having optimum growth pH of about 8.1 to about 8.7.

2. A method for the production of methane which comprises the steps of:
   (a) culturing a methanogen in a culture medium containing a first methanogenic substrate selected from the group consisting of methanol and methylamine, then
   (b) culturing the methanogen in a culture medium containing a second methanogenic substrate selected from the group consisting of acetic acid, acetates and hydrogen-carbon dioxide, and
   (c) recovering the methane produced,
   wherein the methanogen is *Methanosarcina alcaliphilum* NY-728 (FERM BP-2309), and the fermentation is carried out at pH of about 8.1 to about 8.7.

3. The method for the production of methane of claim 2 wherein the first methanogenic substrate is methanol.

4. The method for the production of methane of claim 2 where the second methanogenic substrate is acetic acid or acetates.

5. The method for the production of methane of claim 2 wherein the fermentation is carried out at 15° to 45° C.

6. The method for the production of methane of claim 5 wherein the fermentation is carried out at 34° to 42° C.

7. The method for the production of methane of claim 2 wherein the first methanogenic substrate is methanol, the second methanogenic substrate is acetic acid or acetates and the fermentation is carried out at pH of 8.1 to 8.7 at 15° to 45° C.

* * * * *